(12) United States Patent
Roentgen et al.

(10) Patent No.: US 9,970,816 B2
(45) Date of Patent: May 15, 2018

(54) LIGHT SENSOR MODULES AND SPECTROMETERS INCLUDING AN OPTICAL GRATING STRUCTURE

(71) Applicant: Heptagon Micro Optics Pte. Ltd., Singapore (SG)

(72) Inventors: Peter Roentgen, Thalwil (CH); Markus Rossi, Jona (CH)

(73) Assignee: Heptagon Micro Optics Pte. Ltd., Singapore (SG)

( * ) Notice: Subject to any disclaimer, the term of this patent is extended or adjusted under 35 U.S.C. 154(b) by 0 days. days.

(21) Appl. No.: 15/510,316

(22) PCT Filed: Sep. 8, 2015

(86) PCT No.: PCT/SG2015/050308
§ 371 (c)(1),
(2) Date: Mar. 10, 2017

(87) PCT Pub. No.: WO2016/039690
PCT Pub. Date: Mar. 17, 2016

(65) Prior Publication Data
US 2017/0248467 A1 Aug. 31, 2017

Related U.S. Application Data
(60) Provisional application No. 62/049,107, filed on Sep. 11, 2014.

(51) Int. Cl.
*G01J 3/28* (2006.01)
*G01J 3/18* (2006.01)
(Continued)

(52) U.S. Cl.
CPC ............... *G01J 3/18* (2013.01); *G01J 3/0256* (2013.01); *G01J 3/10* (2013.01); *G01J 3/2803* (2013.01);
(Continued)

(58) Field of Classification Search
CPC .................. G01J 3/28; G01J 3/26; G01J 3/44
See application file for complete search history.

(56) References Cited

U.S. PATENT DOCUMENTS 6,226,083 B1   5/2001  Schwerzel et al.
9,228,896 B2 * 1/2016  Lai ........................ G01J 3/1895
(Continued)

FOREIGN PATENT DOCUMENTS

WO   WO 2013/162528   10/2013

OTHER PUBLICATIONS

International Search Report of ISA/AU for PCT/SG2015/050308 (dated Dec. 12, 2015).
(Continued)

*Primary Examiner* — Abdullahi Nur
(74) *Attorney, Agent, or Firm* — Fish & Richardson P.C.

(57) ABSTRACT

An optoelectronic module includes a light guide arranged to receive light, such as ambient light or light reflected by an object. The light guide has a diffractive grating that includes multiple sections, each of which is tuned to a respective wavelength or narrow band of wavelengths. The module further includes multiple photosensitive elements, each of which is arranged to receive light diffracted by a respective one of the sections of the diffractive grating. The module can be integrated, for example, as part of a spectrometer or other apparatus for optically determining characteristics of an object.

22 Claims, 5 Drawing Sheets

(51) Int. Cl.
   *G01N 21/27*   (2006.01)
   *G01J 3/02*    (2006.01)
   *G01N 21/25*   (2006.01)
   *G01J 3/10*    (2006.01)
   *F21V 8/00*    (2006.01)

(52) U.S. Cl.
   CPC ........... *G01N 21/255* (2013.01); *G01N 21/27* (2013.01); *G02B 6/005* (2013.01); *G02B 6/0026* (2013.01); *G02B 6/0055* (2013.01); *G01J 2003/2806* (2013.01); *G01J 2003/2813* (2013.01)

(56) References Cited

U.S. PATENT DOCUMENTS

2007/0167839  A1    7/2007   Carver
   2011/0026022  A1    2/2011   Takizawa et al.
   2011/0112769  A1    5/2011   Niederberger et al.
   2012/0206726  A1    8/2012   Pervez et al.

OTHER PUBLICATIONS

Supplementary European Search Report issued in European Application No. 15839632.5, dated Mar. 20, 2018, 7 pages.

\* cited by examiner

LIGHT SENSOR MODULES AND SPECTROMETERS INCLUDING AN OPTICAL GRATING STRUCTURE

FIELD OF THE DISCLOSURE

This disclosure relates to light sensor modules and spectrometers that include an optical grating structure.

BACKGROUND

Various manufacturing and other processes involve measuring and collecting optical radiation data, in particular spectral emission characteristics, of a source of optical radiation. The manufacturing or other process may be a process for which optical radiation is used as part of performing the process or in which optical radiation is generated by the process. In some instances, such as imaging applications, it may be desirable to measure and determine the spectral emission characteristics of the ambient light.

SUMMARY

The present disclosure describes optoelectronic modules that include an optical grating structure and, in various implementations, may be used for a wide range of applications that involve detecting or measuring the spectral characteristics of optical radiation. The optoelectronic modules can be used in various applications to detect characteristics of ambient light or light reflected by an object.

For example, in one aspect, an optoelectronic module includes a light guide arranged to receive light from outside the module. The light guide has a diffractive grating that includes multiple sections, each of which is tuned to a respective wavelength or narrow band of wavelengths. The module further includes multiple photosensitive elements, each of which is arranged to receive light diffracted by a respective one of the sections of the diffractive grating.

In another aspect, a method of analyzing composition of light includes receiving the light, separating the received light into its spectral components and directing the separated spectral components along a light guide. The method further includes using a diffractive grating formed in the light guide to diffract each of a plurality of wavelengths or narrow bands of wavelengths from among the spectral components to respective photosensitive elements, each of which is associated, respectively, with a particular one of the wavelengths or narrow bands of wavelength.

Some implementations include one or more of the following features. For example, different sections of the diffractive grating can have periodic grating structures that differ from one another. The diffractive grating can comprise, for example, sub-wavelength structures or multi-layer coated grating structures. The diffractive grating can be disposed, for example, on a sensor-side of the light guide.

In some cases, the optoelectronic module further includes an optical assembly arranged to receive the light, wherein the light guide has at least one other diffractive grating arranged to diffract the received light into its spectral components. In some instances, the at least one other diffractive grating includes a first diffractive grating disposed on an optical assembly-side of the light guide, and a second diffractive grating disposed to intersect a zeroth-order light beam passing through the first diffractive grating.

The photosensitive elements in the module can be implemented, for example, as pixels in a CMOS or CCD sensor. In some cases, the photosensitive elements are implemented as discrete light sensors.

The optoelectronic module can include means to prevent stray light from adjacent optical channels from being sensed by the photosensitive elements. For example, in some cases, one or more respective color filters are present over at least some of the photosensitive elements. In some instances, opaque spacers separate the photosensitive elements from one another.

The disclosure also describes an apparatus (e.g., a spectrometer) for optically determining characteristics of an object. The apparatus includes an emitter operable to generate light at one or more particular wavelengths or ranges of wavelengths, and a module to detect light reflected by an object. The module can include a light guide arranged to receive at least some of the light reflected by the object, the light guide having a diffractive grating that includes a plurality of sections each of which is tuned to a respective wavelength or narrow band of wavelengths. The module further includes a plurality of photosensitive elements each of which is arranged to receive light diffracted by a respective one of the sections of the diffractive grating. Additional features of the module as described in this disclosure also can be incorporated in some implementations.

In some implementations, the apparatus further includes an optical component arranged to direct at least some of the light generated by the emitter toward the module. In some instances, the optical component is movable such that when the optical component is in a first position, light from the emitter is directed by the optical component toward the module, and when the optical component is in a second position, light from the emitter is directed by the optical component toward the object.

Various implementations include one or more of the following advantages. For example, the module can provide a relatively compact and cost efficient way to detect the spectral components of ambient or other light or to detect characteristics of an object optically.

Other aspects, features and advantages will be readily apparent from the following detailed description, the accompanying drawings, and the claims.

DETAILED DESCRIPTION

Figure 1:
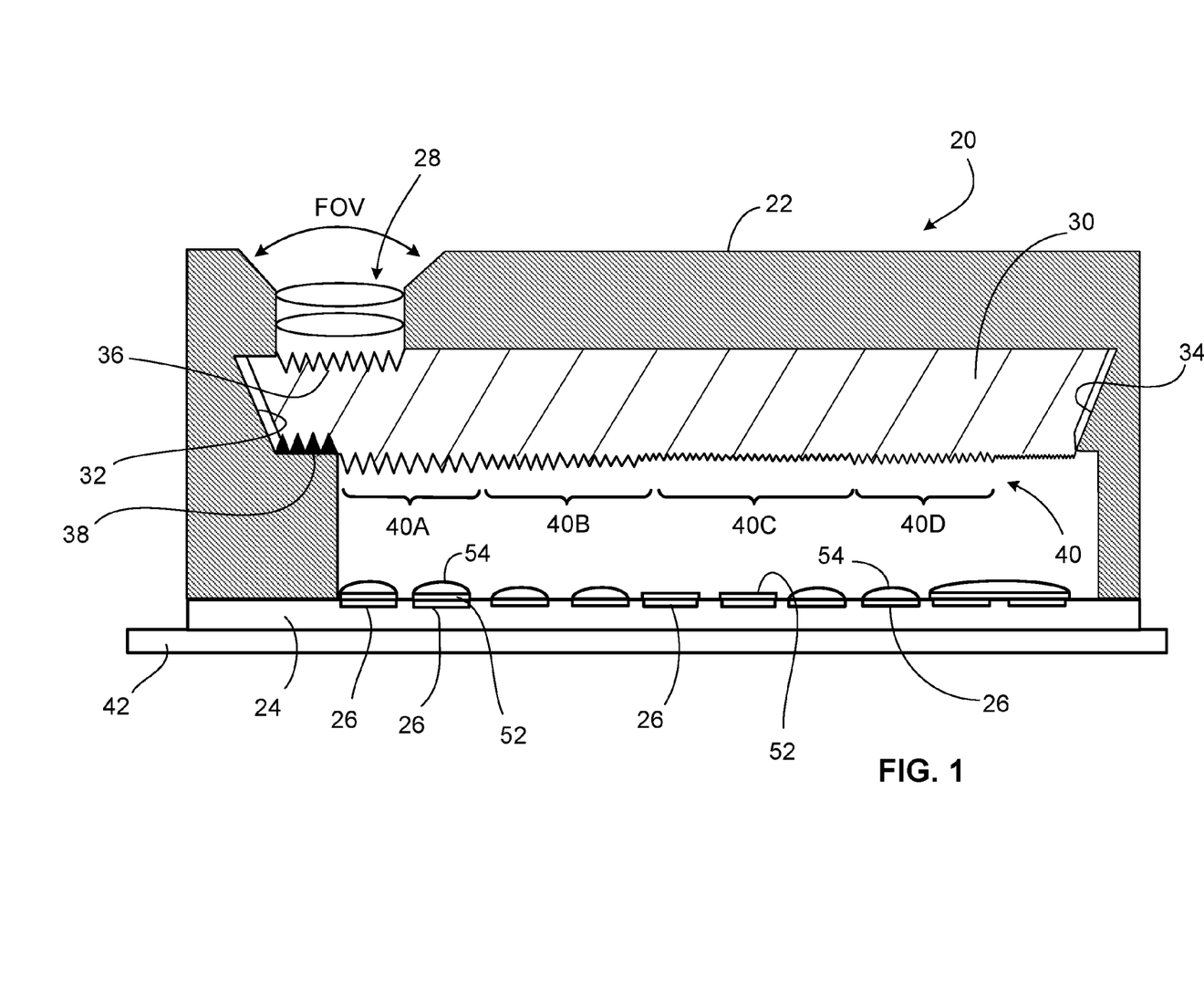
FIG. 1 illustrates an example of an optoelectronic module.

As illustrated in FIG. 1, an optoelectronic module 20, which is operable as a compact spectrometer, includes a housing 22 whose walls in some implementations are substantially opaque or non-transparent to light of particular wavelengths or ranges of wavelengths. The light may be ambient light that comes from any one or more of various sources, such as the sun, indoor or outdoor lighting, sodium vapor lamps, light emitting diodes (LEDs) or other sources of visible and/or non-visible light. In some instances, light may be directed onto an object via an emitter associated with the module 20 and reflected off of the object. For example, in some cases, a comparison between the light emitted and the light reflected back to the optoelectronic module 20 (i.e., the light absorbed by the object) can provide important information about the object. In some implementations, the module 20 functions as a spectrometer that can generate and detect radiation in the visible, infra-red ("IR"), near-infrared ("near IR"), and/or other parts of the spectrum.

The housing 22 has an opening in which an optical assembly 28 is disposed. The optical assembly 28 can include one or more lenses, prisms, or other beam shaping optical elements, and can have a relatively wide field-of-view (FOV) (e.g., equal to or greater than 120°). The module 20 further includes a light guide 30 to guide the received light to a light sensor 24. The light guide 30 can be composed, for example, of glass or another substantially transparent material.

The light sensor 24 can be implemented, for example, as a silicon CMOS or CCD sensor having multiple photosensitive elements (i.e., pixels) 26, each of which is arranged to detect, respectively, a different part of the spectrum (i.e., different wavelength or narrow range of wavelengths). The sensor 24 can include, for example, an array of pixels organized in a two-dimensional grid. In a particular implementation, the CMOS sensor pixel array may have dimensions of 100×100 pixels. The sensor 24 can be mounted, for example, on a substrate such as a printed circuit board (PCB) 42.

Figure 2:
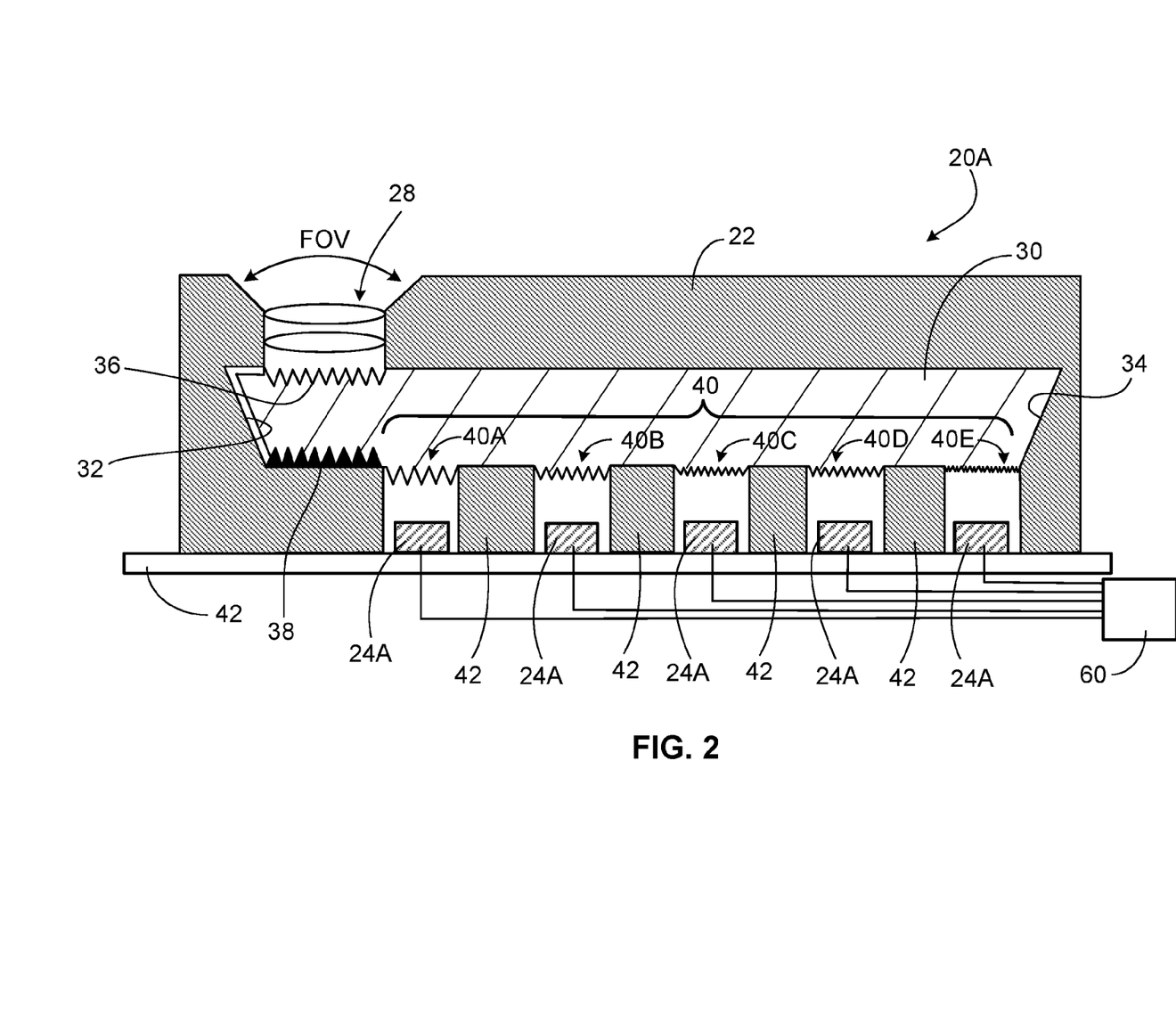
FIG. 2 illustrates another example of an optoelectronic module.

In an alternative implementation, as shown in FIG. 2, instead of a CMOS or CCD sensor having multiple pixels 26, a module 20A can include discrete light sensors 24A such as photodiodes as the photosensitive elements. Further, in some instances, the sensor 24 is sensitive to the near IR and be implemented, for example, using GaAs-based sensors. The sensors 24A can be mounted on a substrate such as a printed circuit board (PCB) 42.

The housing 22 can be attached, for example, to the sensor-side of the sensor 24 (see FIG. 1) or the PCB 42 (see FIG. 2). The non-transparent material of the housing 22 can comprise, for example, a polymer material (e.g., epoxy, acrylate, polyurethane, or silicone) containing a non-transparent filler (e.g., carbon black, a pigment, an inorganic filler, or a dye). As used in this disclosure, the terms "opaque," "transparent" and "non-transparent" are made with reference to the particular wavelength(s) detectable by the photosensitive parts of the sensor 24 in the module. Thus, a particular feature, for example, may be considered "non-transparent" even though it may allow light of other wavelengths to pass through.

Figure 3:
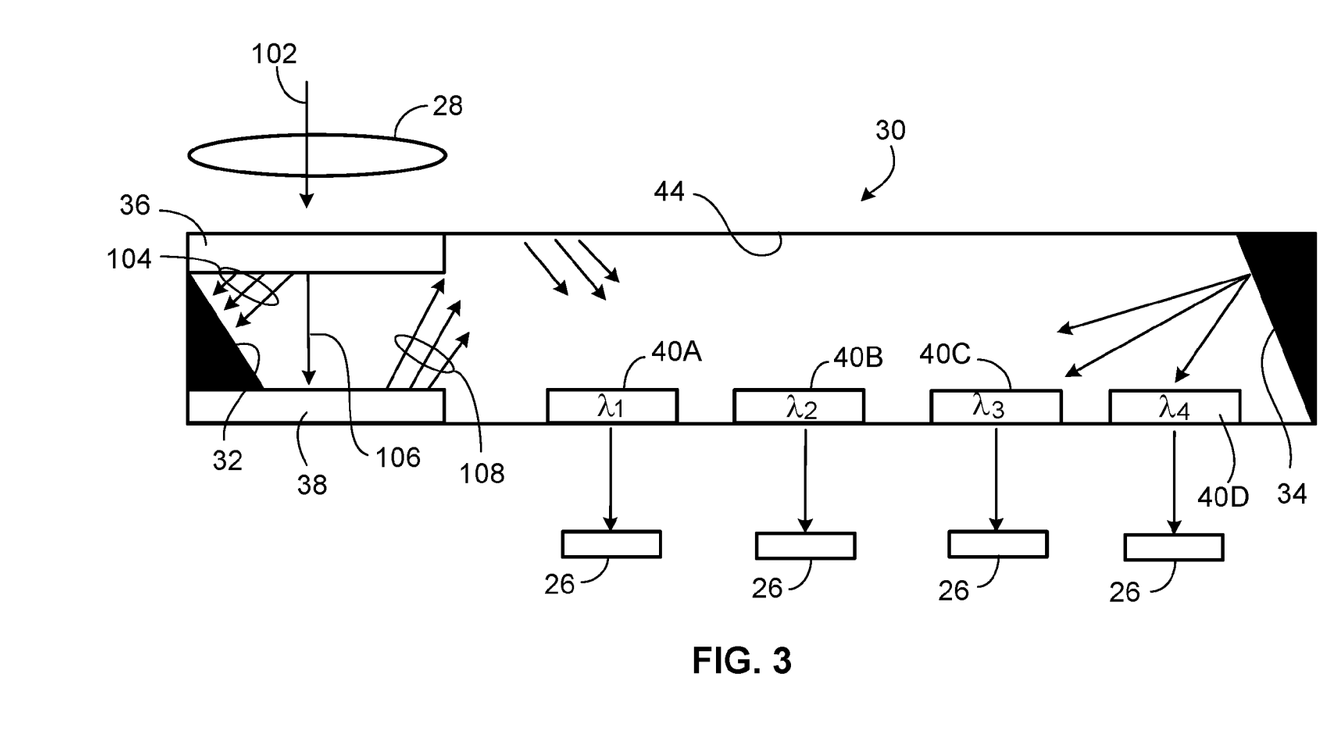
FIG. 3 illustrates examples of light beams traveling in a light guide.

As illustrated in the examples of FIGS. 1 and 2, the light guide 30 has reflective angled surfaces 32, 34 and diffraction gratings 36, 38, 40. As shown in FIG. 3, the first grating 36 can be formed at the optical assembly-side of the light guide 30, whereas the second grating 38 is formed at the sensor-side of the light guide 30. The first and second diffraction gratings 36, 38 diffract the incoming light 102 into its spectral components, wherein the spectral components are diffracted with respective diffraction angles, and collectively help direct the light along the light guide 30 to the third diffraction grating(s) 40. In particular, the first grating 36, which can be implemented for example as a square wave grating, diffracts the incoming light 102 into beams of various diffraction orders m=0, +1, +2, etc. Beams 104 of order m>|1| may be diffracted toward the inclined surface 32, which reflects the beams along the light guide 30 preserving the diffraction angles of the respective spectral components. Beams 106 of order m=0 travel toward the second grating 38, which also can be implemented, for example, as a square wave grating. The second grating 38 diffracts the beam 106 into its spectral components 108 wherein the spectral components are diffracted with respective diffraction angles. As the beams 104, 108 travel along the light guide 30, they may be reflected by the surface 44 of the light guide 30 and/or the reflective surface 34 at the far end of the light guide 30 such that the diffraction angles of the respective spectral components are preserved.

The third grating(s) 40 is formed in the sensor-side of the light guide 30 and diffracts the particular wavelengths of interest to respective ones of the photosensitive elements 26 (FIG. 1) or photodiodes 24A (FIG. 2). The third grating 40 can be implemented, for example, as a continuously varying diffracting grating in which the period and/or the profile shape of the grating structure varies such that each section (e.g., 40A, 40B, 40C, 40D, 40E) of the grating is tuned to a particular wavelength or narrow band of wavelengths. That is, the grating structures 40A, 40B, 40C, 40D, 40E are configured such that their respective coupling efficiencies are optimized to a particular incidence angle and wavelength of incident light. The third grating 40 can be implemented, for example, as a sub-wavelength structure or as multi-layer coated grating structures. In general, each section 40A, 40B, etc. of the third grating 40 can be selective to a wavelength (or narrow band of wavelengths) and a particular incidence angle that differs from section to section. Thus, as illustrated in FIG. 3, the first section 40A of the grating 40 is tuned to a first wavelength $\lambda 1$ (or narrow range of wavelengths), the second section 40B is tuned to a different second wavelength $\lambda 2$ (or narrow range of wavelengths), the third section 40C is tuned to yet another wavelength $\lambda 3$ (or narrow range of wavelengths), and the fourth section 40D is tuned to still another wavelength $\lambda 4$ (or narrow range of wavelengths).

In some instances, each section of the third grating 40 may be tuned, for example, to a narrow range of wavelengths having a resolution of at least ten nanometers. Collectively, the various sections of the grating 40 can cover, for example, substantially the entire visible spectral range from 400 nm-700 nm, and in some instances, may cover parts of the UV or IR parts of the spectrum.

Figure 4A:
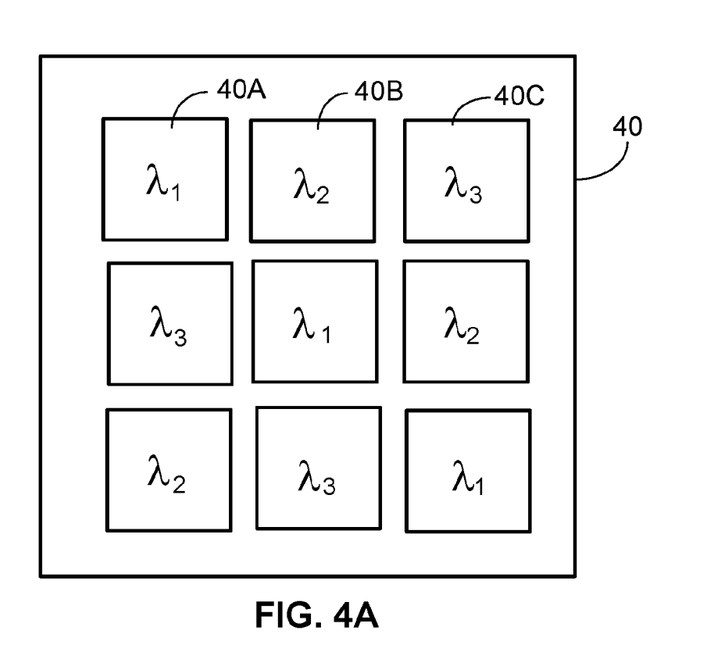
FIGS. 4A and 4B illustrate examples of bottom views of grating structures on the sensor-side of the light guide.
Figure 4B:
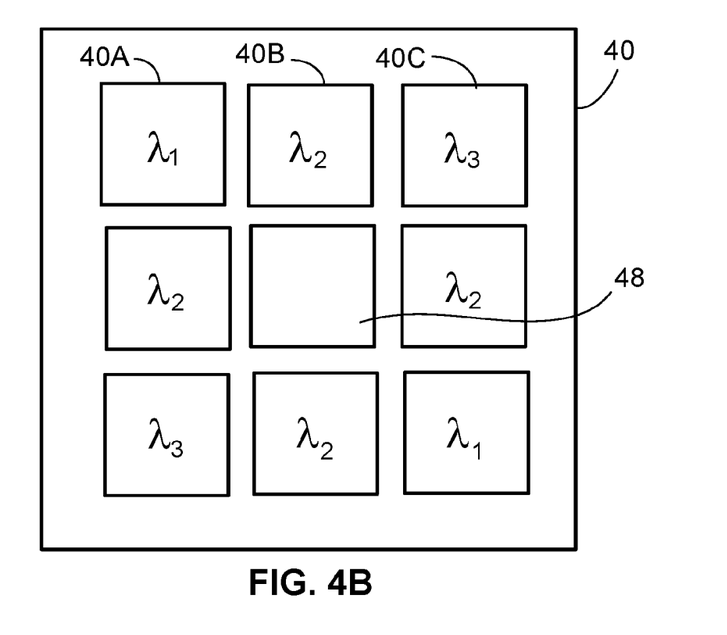

In some cases, multiple sections of the grating 40 may be tuned to the same wavelength (or narrow band of wavelengths). For example, as illustrated in FIG. 4A, some sections of the grating 40 are tuned to the first wavelength $\lambda 1$, some sections of the grating 40 are tuned to the second wavelength $\lambda 2$, and some sections of the grating 40 are tuned to the third wavelength $\lambda 3$. The number of sections tuned to each particular wavelength (or narrow band of wavelengths) need not be the same. Thus, as shown in the example of FIG. 4B, the number of sections of the grating 40 tuned to the second wavelength $\lambda 2$ is greater than the number of sections tuned to the first wavelength $\lambda 1$ or the third wavelength $\lambda 3$. Further, some sections of the surface of the light guide 30 on which the third grating 40 is formed may not include a grating structure and, therefore, may not be selective for any particular wavelength. For example, as shown in FIG. 4B, the region 48 of the light guide surface does not include a grating structure and, therefore, is not dedicated to particular wavelength or narrow range of wavelengths.

Depending on the implementation, one or more photosensitive elements 26 (FIG. 1) or 24A (FIG. 2) are arranged directly below each respective section 40A, 40B, etc. of the grating 40. Each section 40A, 40B, etc. of the grating 40 is arranged such that beams of light having the wavelength for which the particular grating section is tuned are diffracted to the underlying photosensitive elements. Thus, each photosensitive element 26 or 24A is associated with a particular wavelength (or narrow band of wavelengths). A photosensitive element can be positioned directly below each section 48 of the light guide 30. Since such sections 48 are not tuned to a particular wavelength, the photosensitive elements that detect the light passing through those sections can be used to detect the overall level of ambient light.

To help prevent stray light from adjacent channels being incident on the photosensitive elements 26, color filters 52 can be provided over some or all of the photosensitive elements 26 (see FIG. 1). In some cases, microlenses 54 can be provided over some or all of the photosensitive elements 26 to help focus the light onto the respective pixels. As illustrated in FIG. 2, instead of (or in addition to) providing color filters 52 over the photosensitive elements, substantially opaque spacers 44 can be provided to separate adjacent optical channels from one another and help prevent optical cross-talk between the different channels. The spacers 44 can be composed, for example, of the same material as the housing 22.

Control and processing circuitry 60 is arranged to read out signals from the photosensitive elements 26 (or 24A). Outputs signals from the photosensitive elements (i.e., the pixels 26 (FIG. 1) or the discrete detectors 24A (FIG. 2)) are thus provided to control and processing circuitry 60 (see FIG. 2), which is configured to process the photocurrents and identify the corresponding wavelength(s) in the incident light based on which photosensitive element generated each particular output signal. The control and processing circuitry 60 can include memory that stores a table associating each photosensitive element 26 (or 24A) with a corresponding wavelength (or narrow wavelength band). The processing circuitry 60 can use the information in the table to determine the corresponding wavelength (or narrow wavelength band) associated with a signal received from any one of the photosensitive elements 26 (or 24A). The control and processing circuitry 60 can generate output (e.g., text of graphics) indicative of the absolute or relative amounts of incident light detected by the module for each wavelength or narrow band of wavelengths. The output generated by the circuitry 60 can then be displayed, for example, on a display device, such as the display screen of a computing device (e.g., laptop).

The control and processing circuitry 60 can be implemented, for example, as one or more integrated circuits in one or more semiconductor chips with appropriate digital logic and/or other hardware components (e.g., read-out registers; amplifiers; analog-to-digital converters; clock drivers; timing logic; signal processing circuitry; and/or microprocessor). The processing circuitry is, thus, configured to implement and perform the various functions associated with such circuitry. The control and processing circuitry 60 may be external to the module 20 (or 20A). In some cases, the control and processing circuitry 60 can be mounted on the PCB substrate 42.

In some implementations, the level of efficiency of the third diffractive grating 40 may permit, for example, up to 10 nm, or even 20 nm, deviation of diffracted wavelength. In some instances, less deviation may be desirable.

The foregoing techniques may be applicable in a wide range of applications, including semiconductor processing where monitoring of spectral emission characteristics of the ambient environment may be required or tuning of a radiation source may be needed. The techniques also may be useful in spectrometry application. Further, the techniques also can be advantageous in imaging applications, where it may be desirable to measure and determine the spectral emission characteristics of the ambient light.

Figure 5A:
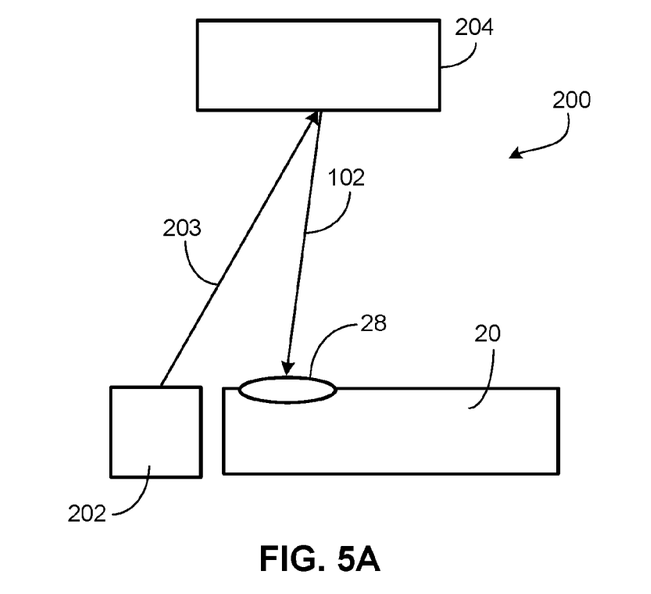
FIGS. 5A and 5B illustrate examples of spectrometers including an optoelectronic module

FIG. 5A illustrates an example of a spectrometer 200 that includes the module 20 (or 20A). The spectrometer 200 also includes an emitter 202 operable to emit beams of light 203 of a known wavelength or range of wavelengths toward an object 204. The emitter 202 can be implemented, for example, by one or more LEDs. If multiple LEDs are provided, some of the LEDs can generate light of a wavelength different from other LEDs. Based on the light reflected back toward the module 20 (or 20A), the module can detect which wavelength(s) were absorbed by the object 204. In other implementations the emitter can be a white-light source. An analysis of the light reflected back to the module (i.e., the light that is absorbed by the object) can provide information about the object 204, such as its color.

Figure 5B:
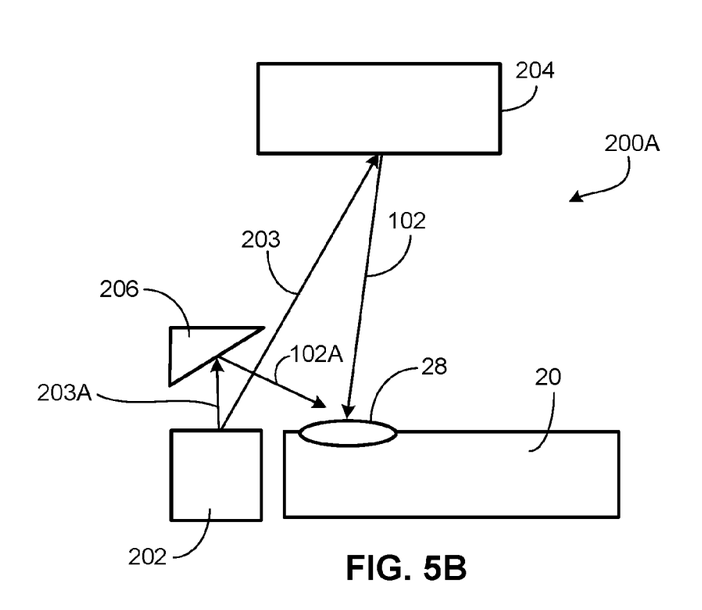

As shown in FIG. 5B, in some instances, the spectrometer 200A can include an optical component 206 that directs some of the light 203A emitted by the emitter 202 toward the module 20 (or 20A). The optical component 206 can include, for example, any number of refractive, diffractive, and/or reflective optical elements. Further, in some implementations, the optical component 206 is actuate-able such that it can be moved between two or more positions. At a first instant, with the optical component 206 in a first position, light 102A can be reflected from the optical component 206 to the optoelectronic module 20 (or 20A). Then, the optical component 206 can be repositioned at another instant such that light 203 is incident on the object 204. The optoelectronic module 20 (or 20A) can collect the light 102 reflected from the object 204. The modules 20 or 20A thus can be integrated for use with a beam splitter for spectrometry/spectroscopy applications. The data collected by the module 20 (or 20A) at the two instances can be compared, and the wavelengths of light absorbed by the object 204 can be identified to provide information about the object.

Various modifications can be made within the spirit of the foregoing disclosure. Thus, other implementations are within the scope of the claims.

What is claimed is:

1. An optoelectronic module comprising:
    an optical assembly arranged to receive light from outside the module,
    a light guide to receive the light from the optical assembly;
    a first diffractive grating disposed on an optical assembly-side of the light guide, and a second diffractive grating disposed so as to intersect a zeroth-order light beam passing through the first diffractive grating, wherein the first and second diffractive gratings are arranged to diffract the light into its spectral components,
    the light guide having a third diffractive grating that includes a plurality of sections each of which is tuned to a respective wavelength or narrow band of wavelengths of the spectral components; and
    a plurality of photosensitive elements each of which is arranged to receive light diffracted by a respective one of the sections of the third diffractive grating.

2. The optoelectronic module of claim 1 wherein different sections of the third diffractive grating have periodic grating structures that differ from one another.

3. The optoelectronic module of claim 1 wherein the third diffractive grating comprises sub-wavelength structures or multi-layer coated grating structures.

4. The optoelectronic module of claim 1 wherein the photosensitive elements are pixels in a CMOS or CCD sensor.

5. The optoelectronic module of claim 1 wherein the photosensitive elements are discrete light sensors.

6. The optoelectronic module of claim 1 further including means to prevent stray light from adjacent optical channels from being sensed by the photosensitive elements.

7. The optoelectronic module of claim 1 further including one or more respective color filters over at least some of the photosensitive elements.

8. The optoelectronic module of claim 1 further including opaque spacers separating the photosensitive elements from one another.

9. The optoelectronic module of claim 1 wherein the third diffractive grating is disposed on a sensor-side of the light guide.

10. A method of analyzing composition of light, the method comprising:
receiving the light in an optoelectronic module;
separating the received light into its spectral components using a first diffractive grating and a second diffractive grating, wherein the second diffractive grating intersects a zeroth-order light beam received from the first diffractive grating;
directing the separated spectral components along a light guide; and
using a third diffractive grating to diffract each of a plurality of wavelengths or narrow bands of wavelengths from among the spectral components traveling in the light guide to respective photosensitive elements, each of which is associated, respectively, with a particular one of the wavelengths or narrow bands of wavelength.

11. The method of claim 10 further including providing an output indicative of respective amounts of the light in each of the wavelengths or narrow bands of wavelength.

12. An apparatus for optically determining characteristics of an object, the apparatus comprising:
an emitter operable to generate light at one or more particular wavelengths or ranges of wavelengths;
a module operable to detect incoming light; and
a movable optical component, wherein when the optical component is in a first position,
light from the emitter is directed by the optical component toward the module as the incoming light, and when the optical component is in a second position, light from the emitter is incident on the object such that the object reflects at least some of the incident light toward the module as the incoming light, and
wherein the module comprises:
a light guide arranged to receive the incoming light, the light guide having a diffractive grating that includes a plurality of sections each of which is tuned to a respective wavelength or narrow band of wavelengths; and
a plurality of photosensitive elements each of which is arranged to receive light diffracted by a respective one of the sections of the diffractive grating.

13. The apparatus of claim 12 wherein different sections of the diffractive grating have periodic grating structures that differ from one another.

14. The apparatus of claim 12 wherein the diffractive grating comprises sub-wavelength structures or multi-layer coated grating structures.

15. The apparatus of claim 12 wherein the module further included an optical assembly arranged to receive light from outside the module, wherein the light guide has at least one other diffractive grating arranged to diffract the received light into its spectral components.

16. An apparatus for optically determining characteristics of an object, the apparatus comprising:
an emitter operable to generate light at one or more particular wavelengths or ranges of wavelengths, at least some of the light being directed toward the object;
a module including:
an optical assembly arranged to receive light reflected by the object, the object being outside the module;
a light guide to receive the light from the optical assembly;
a first diffractive grating disposed on an optical assembly-side of the light guide, and a second diffractive grating disposed so as to intersect a zeroth-order light beam passing through the first diffractive grating, wherein the first and second diffractive gratings are arranged to diffract the light into its spectral components, the light guide having a third diffractive grating that includes a plurality of sections each of which is tuned to a respective wavelength or narrow band of wavelengths of the spectral components; and
a plurality of photosensitive elements each of which is arranged to receive light diffracted by a respective one of the sections of the third diffractive grating.

17. The apparatus of claim 16 wherein the photosensitive elements are pixels in a CMOS or CCD sensor.

18. The apparatus of claim 16 wherein the photosensitive elements are discrete light sensors.

19. The apparatus of claim 16 wherein the module further includes means to prevent stray light from adjacent optical channels from being sensed by the photosensitive elements.

20. The apparatus of claim 16 further including one or more respective color filters over at least some of the photosensitive elements.

21. The apparatus of claim 16 further including opaque spacers separating the photosensitive elements from one another.

22. The apparatus of claim 16 wherein the third diffractive grating is disposed on a sensor-side of the light guide.

* * * * *